United States Patent [19]

Mehlhorn et al.

[11] Patent Number: 4,826,842
[45] Date of Patent: May 2, 1989

[54] AGENTS AGAINST FISH PARASITES

[75] Inventors: Heinz Mehlhorn, Neuss-Üdesheim; Günter Schmahl, Bochum, both of Fed. Rep. of Germany

[73] Assignee: Bayer Aktiengesellschaft, Leverkusen, Fed. Rep. of Germany

[21] Appl. No.: 149,048

[22] Filed: Jan. 27, 1988

[30] Foreign Application Priority Data

Feb. 3, 1987 [DE] Fed. Rep. of Germany ....... 3703103

[51] Int. Cl.$^4$ ............................................ A01N 43/66
[52] U.S. Cl. .................................................. 514/241
[58] Field of Search .......................................... 514/241

[56] References Cited

U.S. PATENT DOCUMENTS 3,970,752  7/1976  Atchinger et al. ................... 514/241
4,219,552  8/1980  Haberkorn et al. .................. 514/241

FOREIGN PATENT DOCUMENTS 3300793  7/1984  Fed. Rep. of Germany ...... 514/241
3408768  9/1985  Fed. Rep. of Germany ...... 514/241
3418431  11/1985  Fed. Rep. of Germany ...... 514/241

Primary Examiner—Allen J. Robinson
Attorney, Agent, or Firm—Sprung Horn Kramer & Woods

[57] ABSTRACT

A method of combating ectoparasites in fish which comprises applying to such fish or to water in which said fish are or will be swimming an ectoparasiticidally effective amount of a triazinetrione of the formula

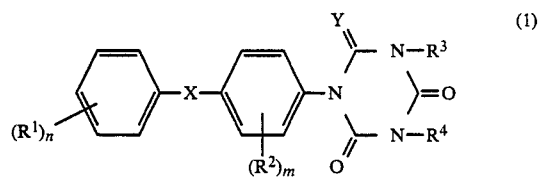

in which
X is O or S,
Y is O or S,
$R^1$ and $R^2$ each independently is a radical from the group consisting of halogen, nitro, CN, amino, alkyl, halogenoalkyl, alkoxy, halogenoalkoxy, alkylthio, halogenoalkylthio, alkylsulphonyl, alkylsulphinyl, halogenoalkylsulphonyl, halogenoalkylsulphinyl, acyl, carboxy, carbonylamino, carbonylalkoxy, carbamoyl and sulphamoyl,
n and m each independently is an integer from 0 to 3, and
$R^3$ and $R^4$ each independently is hydrogen or alkyl.

5 Claims, No Drawings

AGENTS AGAINST FISH PARASITES

The present invention relates to agents containing triazinetriones against parasitic protozoa and metazoa in fish.

The protozoa and metazoa include classes which are widespread as parasites in fish. They are a serious problem in the husbandry of fattening animals in large breeding units because an infestation can rapidly spread over the entire stock.

Some parasitic protozoa and metazoa accumulate on the skin and gills of the fish and thereby cause damage to the skin through which the fish become susceptible to infections. They are also vectors for virus infections. Other parasitic protozoa and metazoa infest the internal organs of fish, for example the intestine and bones, and lead to deformities or to the death of the fish.

Agents for combating parasitic protozoa and metazoa are known, but they are not always completely satisfactory. In addition, they usually have only a narrow action spectrum.

It has been found that the known triazinetriones of the formula (I)

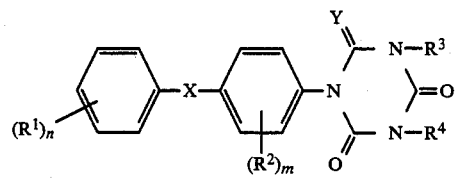

in which
X represents O or S,
Y represents O or S,
the symbols $R^1$ represent identical or different radicals from the group comprising halogen, nitro, CN, amino, alkyl, halogenoalkyl, alkoxy, halogenoalkoxy, alkylthio, halogenoalkylthio, alkylsulphonyl, alkylsulphinyl, halogenoalkylsulphonyl, halogenoalkylsulphinyl, acyl, carboxyl, carbonylamino, carbonylalkoxy, carbamoyl and sulphamoyl, the symbols $R^2$ represent identical or different radicals from the group of substituents mentioned for $R^1$,
n and m represent integers from 0 to 3,
$R^3$ represents hydrogen or alkyl and
$R^4$ represents hydrogen or alkyl,
can be used for combating ectoparasites in fish.

The compounds of the formula (I) are known or can be prepared by methods which are known per se (DE-OS (German Published Specification) No. 2,413,722; DE-OS (German Published Specification) No. 2,718,799 and U.S. Pat. No. 4,219,552).

Preferred compounds of the formula (I) are those in which
X and Y represent O,
$R^1$ and $R^2$ independently of one another represent identical or different radicals from the group comprising halogen, in particular fluorine, chlorine or bromine, nitro, CN, amino, $C_{1-4}$-alkyl, in particular methyl or ethyl, $C_{1-4}$-halogenoalkyl, in particular trifluoromethyl, trichloromethyl or fluoro-chloroethyl, $C_{1-4}$-alkoxy, in particular methylenedioxy, isopropoxy or methoxy, $C_{1-4}$-halogenoalkoxy, in particular trifluoromethoxy, difluoromethylenedioxy or tetrafluoroethylenedioxy, $C_{1-4}$-alkylthio, in particular methylenemercapto or ethylenemercapto, $C_{1-4}$-halogenoalkylthio, in particular trifluoromethylthio, $C_{1-4}$-alkylsulphonyl, in particular methylsulphonyl, $C_{1-4}$-alkylsulphinyl, $C_{1-4}$-halogenoalkylsulphonyl and -sulphinyl, in particular trifluoromethylsulphonyl, $C_{1-4}$-acyl in particular acetyl, propionyl or benzoyl, and $C_{1-4}$-carbonylalkoxy, in particular methoxycarbonyl or ethoxycarbonyl,
n and m represent integers from 0 to 2 and
$R^3$ and $R^4$ independently of one another represent hydrogen or $C_{1-4}$-alkyl, in particular methyl.

Compounds of the formula (I) which are particularly preferably employed are those in which
$R^4$ represents hydrogen,
$R^3$ represents $C_{1-4}$-alkyl,
Y represents oxygen or sulphur,
X represents oxygen,
$R^2$ represents identical or different radicals from the group comprising $C_{1-4}$-alkyl, halogen, such as, in particular, chlorine or bromine, $C_{1-4}$-alkoxy and $C_{1-2}$-halogenoalkyl,
$R^1$ represents identical or different radicals from the group comprising halogen, in particular chlorine or bromine, $NO_2$, $C_{1-4}$-alkyl, $C_{1-2}$-halogenoalkyl, $C_{1-4}$-alkylmercapto, which is optionally substituted by halogen, $C_{1-4}$-alkoxy, which is optionally substituted by halogen, $C_{1-4}$-alkylsulphinyl, which is optionally substituted by halogen, and $C_{1-4}$-alkylsulphonyl, which is optionally substituted by halogen, and
n and m represent integers from 0 to 2.

Particularly preferred compounds of the formula I are those in which
$R^4$ represents hydrogen,
$R^3$ represents methyl,
X and Y represent oxygen,
$R^2$ represents identical or different radicals from the group comprising chlorine, bromine, methyl, trifluoromethyl, methoxy and ethoxy,
$R^1$ represents identical or different radicals, in particular in the 4-position, from the group comprising trifluoromethylmercapto, trifluoromethylsulphinyl, trifluoromethylsulphonyl and trifluoromethoxy, and
n and m independently of one another represent 0 or 1.

The following compounds may be mentioned as examples, without limiting the invention in any way: 1-[3,5-dichloro-4-(4'-trifluoromethoxy-phenoxy)-phenyl]-3-methyl-1,3,5-triazine-2,4,6(1H,3H,5H)-trione, 1-[3,5-dichloro-4-(4'-trifluoromethylthio-phenoxy)-phenyl]-3-methyl-1,3,5-triazine-2,4,6(1H,3H,5H)-trione, 1-[4-(4'-trifluoromethylthio-phenoxy)-phenyl]-3-methyl-1,3,5-triazine-2,4,6(1H,3H,5H)-trione, 1-[3-chloro-5-bromo-4-(4'-trifluoromethylthio-phenoxy)-phenyl]-3-methyl-1,3,5-triazine-2,4,6(1H,3H,5H)-trione, 1-[3,5-dibromo-4-(4'-trifluoromethylthio-phenoxy)-phenyl]-3-methyl-1,3,5-triazine-2,4,6(1H,3H,5H)-trione, 1-[3,5-dichloro-4-(3'-methyl-4'-trifluoromethylthio-phenoxy)-phenyl]-3-methyl-1,3,5-triazine-2,4,6(1H,3H,5H)-trione, 1-[4-(4'-trifluoromethylsulphonyl-phenoxy)-phenyl]-3-methyl-1,3,5-triazine-2,4,6(1H,3H,5H)-trione, 1-[3,5-dichloro-4-(4'-trifluoromethylsulphonyl-phenoxy)-phenyl]-3-methyl-1,3,5-triazine-2,4,6(1H,3H,5H)-trione, 1-[3-chloro-5-bromo-4-(4'-trifluoromethylsulphonyl-phenoxy)-phenyl]-3-methyl1,3,5-triazine-2,4,6(1H,3H,5H)-trione, 1-[3,5-dichloro-4-(2'-chloro-4'-trifluoromethylsulphonyl-phenoxy)-phenyl]-3-methyl-1,3,5-triazine-2,4,6(1H,3H,5H)-trione, 1-[3-methoxy-4-(4'-trifluoromethylthio-phenoxy)-phenyl]-3-methyl-1,3,5-triazine-2,4,6-(1H,3H,5H)-trione, 1-[4-(4'-trifluoromethylsulphinyl-phenoxy)-phenyl]-3-methyl-1,3,5-triazine- 2,4,6(1H,3H,5H)-trione, 1-[3,5-dichloro-4-(4'-trifluoromethylsulphinyl-phenoxy)-phenyl]-3-methyl-1,3,5-triazine-2,4,6(1H,3H,5H)-trione, 1-[4-(3'-trifluoromethylsulphonyl-phenoxy)-3,5-dimethylphenyl]-3-methyl-1,3,5-triazine-2,4,6(1H,3H,5H)-trione, 1-[3-chloro-4-(4'-trifluoromethylsulphonyl-phenoxy)-phenyl]-3-methyl-1,3,5-triazine-2,4,6(1H,3H,5H)-trione, 1-[3-methyl-4-(4'-trifluoromethylthio-phenoxy)-phenyl]-3-methyl-1,3,5-triazine-2,4,6-(1H,3H,5H)-trione, 1-[3,5-dichloro-4-(2'-methyl-4'-trifluoromethylsulphonyl-phenoxy)-phenyl]-3-methyl-1,3,5-triazine-2,4,6(1H,3H,5H)-trione, 1-[3-chloro-5-methyl-4-(2'-chloro-4'-trifluoromethylsulphonyl-phenoxy)-phenyl]-3-methyl-1,3,5-triazine-2,4,6(1H,3H,5H)-trione, 1-[4-(4'-trifluoromethylsulphonyl-phenoxy)-3,5-dimethyl-phenyl]-3-methyl-1,3,5-triazine-2,4,6(1H,3H,5H)-trione, 1-[3-chloro-5-methyl-4-(4'-trifluoromethylsulphonyl-phenoxy)phenyl]-3-methyl-1,3,5-triazine-2,4,6(1H,3H,5H)-trione, 1-[3-chloro-4-(2'-chloro-4'-trifluoromethylthio-phenoxy)phenyl]-3-methyl-1,3,5-triazine-2,4,6(1H,3H,5H)-trione, 1-[3-bromo-4-(4'-trifluoromethylsulphonyl-phenoxy)-phenyl]-3-methyl-1,3,5-triazine-2,4,6(1H,3H,5H)-trione, 1-[3-chloro-5-trifluoromethyl-4-(4'-trifluoromethylsulphonylphenoxy)-phenyl]-3-methyl-1,3,5-triazine-2,4,6(1H,3H,5H)trione, 1-[3,5-dichloro-4(4'-trifluoromethylsulphonylphenoxy)-phenyl]-3-methyl-2-thioxo-4,6-dioxo-1,3,5(1H,3H, 5H)-triazine, 1-[3-methyl-4-(4'-trifluoromethylthiophenoxy)-phenyl]-3-methyl-2-thioxo-4,6-dioxo-1,3,5-(1H, 3H,5H)-triazine and 1-[3-methyl-4-(6-trifluoromethyl-benzothiazol-2-yloxy)-phenyl]-3-methyl-1,3,5-triazine-2,4,6-(1H,3H,5H)-trione.

Toltrazuril, the common name for 1-[3-methyl-4-(4'-trifluoromethylthio-phenoxy)-phenyl]-3-methyl-1,3,5-triazine-2,4,6(1H,3H,5H)-trione, may be particularly singled out.

It was known that the triazinetriones of the formula (I) can be used for combating Coccidiae in mammals and poultry. Nothing was known of the fact that they can also be used for combating parasites in fish.

The parasites in fish include, from the strain of the protozoa, species of the class Ciliata, for example *Ichthyophthirius multifiliis, Chilodonella cypini,* Trichodina spp., Glossatella spp. and Epistylis spp., of the class Myxosporidia, for example *Myxosoma cerebralis,* Myxidium, Myxobolus, Hemeguya and Hoterellus, of the class of Microsporidia, for example Glugea spp., Thelohania spp. and Pleistophora spp., and from the strain of Plathelminthes, Monogenea, for example Dactylogyrus spp., Gyrodactylus spp., Pseudodactylogyrus spp. and Diplozoon spp.

The fish include stock, breeding, aquarium and ornamental fish of all age levels which live in fresh water and salt water. The stock and breeding fish include, for example, carp, eels, trout, whitefish, salmon, bream, roach, rudd, chub, sole, plaice, halibut, Japanese yellowtail (*Seriola quinqueradiata*), Japanese eel (*Anguilla japonica*), red seabream (*Pagurus major*), sea bass (*Dicentrarchus labrax*), grey mullet (*Mugilus cephalus*), pompano, gilthread seabream (*Sparus auratus*), Tilapia spp., Chichlides species, such as, for example, Plagioscion, and Channel catfish. The agents according to the invention are particularly suitable for the treatment of fry, for example carp with a body length of 2-4 cm. The agents are also particularly suitable in the fattening of eels.

The fish are treated either orally, for example via the food, or by short-term treatment, a "medical bath" into which the fish are placed and in which they are kept for a period of time (minutes up to several hours), for example on transfer from one breeding basin to another.

However, temporary or continuous treatment of the environment of the fish, for example entire pond systems, aquaria, tanks or basins in which the fish are kept, is also possible.

The active compound is administered in formulations suitable for their use.

Formulations for oral use are powders, granules, solutions and emulsion or suspension concentrates, which are mixed homogeneously with the food as food additives.

The formulations are prepared in a manner which is known per se by mixing the active compound with solid or liquid carriers, if appropriate with the addition of other active compounds, such as emulsifying or dispersing agents, solubilizing agents, dyestuffs, antoxidants and preservatives.

The solid carriers include, for example, natural rock powders, such as kaolins, clays, talc, chalk and diatomaceous earth, organic carriers, such as sugars, sucrose, lactose and glucose, cereal products, such as cereal flours or shredded cereals, starch, animal flours, cellulose and milk powder, and inorganic carriers, such as sodium chloride, carbonates, such as calcium carbonate, bicarborates, aluminium oxides, silicic acid and silicates.

The liquid carriers and solubilizing agents include: water, alkanols, such as ethanol and isopropanol, glycols, such as ethylene glycol, propylene glycol, polyethylene glycols, polypropylene glycols and their copolymers, glycerol, aromatic alcohols, such as benzyl alcohol, phenylethanol and phenoxyethanol, esters, such as ethyl acetate, butyl acetate and benzyl benzoate, ethers, such as alkylene glycol alkyl ethers, such as dipropylene glycol monomethyl ether and diethylene glycol monobutyl ether, ketones, such as acetone and methyl ethyl ketone, aromatic and/or aliphatic hydrocarbons, vegetable or synthetic oils, dimethylformamide, dimethyl sulphoxide, dimethylacetamide, N-methylpyrrolidone and 2-dimethyl-4-oxymethylene-1,3-dioxalone.

The dispersing and emulsifying agents include: non-ionic surfactants, such as polyoxyethylated castor oil, polyoxyethylated sorbitan monooleate, sorbitan monostearate, glycerol monostearate, polyoxyethyl stearate and alkylphenol polyglycol ethers, ampholytic surfactants, such as di-Na N-lauryl-β-iminodipropionate or lecithin, anionic surfactants, such as Na laurylsulphate, fatty alcohol ether-sulphates and mono/dialkyl polyglycol ether-orthophosphate monoethanolamine salt, and cationic surfactants, such as cetyltrimethylammonium chloride.

The concentration of the active compound in the formulations is 1 ppm to 10% by weight.

Preferred formulations for short-term treatment used as a "medical bath", for example for treatment when transferring the fish or for treatment of the environment (pond treatment) of the fish, are solutions of the active compound in one or more polar solvents which give an alkaline reaction on dilution with water.

To prepare the solutions, the active compound is dissolved in a polar water-soluble solvent which either gives an alkaline reaction or to which an alkaline water-soluble substance is added. The latter is advantageously also dissolved in the solvent, but can also be suspended in the solvent and dissolve only in the water. After addition of the active compound solution, the water here should have a pH of 7–10, but preferably a pH of 8–10.

The concentration of the active compound can be in the range from 0.5 to 50%, but preferably in a range from 1 to 25%.

Possible solvents are all the water-soluble solvents in which the active compound is soluble in a sufficient concentration and which are physiologically acceptable.

These are ethyl alcohol, isopropyl alcohol, benzyl alcohol, glycerol, propylene glycol, polyethylene glycols, poly(oxyethylene)-poly(oxypropylene) polymers, basic alcohols, such as mono-, di- and triethanolamine, ketones, such as acetone or methyl ethyl ketone, esters, such as ethyl lactate, and furthermore N-methylpyrrolidone, dimethylacetamide and dimethylformamide, and furthermore dispersing and emulsifying agents, such as polyoxyethylated castor oil, polyethylene glycol sorbitan monooleate, polyethylene glycol stearate, or polyethylene glycol ethers and polyethylene glycol alkylamines.

Bases which may be mentioned for establishing the alkaline pH are organic bases, such as basic amino acids, such as L- and D,L-arginine, L- and D,L-lysine, methylglucosamine, glucosamine and 2-amino-2-hydroxymethylpropane-1,3-diol, and furthermore such as N,N,N',N'-tetrakis-(2-hydroxypropyl)-ethylenediamine or a polyether-tetrol based on ethylenediamine (molecular weight 480-420), and inorganic bases, such as ammonia or sodium carbonate—if appropriate with the addition of water.

The formulations can also contain 0.1 to 20% by weight, preferably 0.1–10% by weight, of other formulation auxiliaries, such as antioxidants, surfactants, suspension stabilizers and thickeners, such as, for example, methylcellulose, alginates, polysaccharides, galactomannanes and colloidal silicic acid. The addition of color, aroma and builder substances for animal nutrition is also possible. Acids which form a buffer system together with the base taken or reduce the pH of the solution may also be mentioned here.

The concentration of the active compound when used depends on the nature and duration of the treatment and the age and condition of the fish treated. It is, for example, 2–50 mg of active compound per liter of water, preferably 5–10 mg per liter, for short-term treatment with a treatment duration of 3–4 hours. In the treatment of young carp, for example, a concentration of 5–10 mg/l is used for a treatment duration of about 1–4 hours. Eels are treated with concentrations of about 5 mg/l for about 4 hours.

For a longer duration of treatment or for continuous treatment, the concentration chosen can be correspondingly lower.

In the case of pond treatments, 0.1–5 mg of active compound per liter of water can be used.

Formulations for use as a food additive have, for example, the following composition:

(a)

Active compound of the formula I: 1–10 parts by weight
Soybean protein: 49–90 parts by weight (b)

Active compound of the formula I: 0.5–10 parts by weight
Benzyl alchol: 0.08–1.4 parts by weight
Hydroxypropylmethylcellulose: 0–3.5 parts by weight
Water: remainder to make up to 100

Formulations for use in "medical baths" and for pond treatment have, for example, the following composition and are prepared as follows:

(c) 2.5 g of toltrazuril are dissolved in 100 ml of triethanolamine, with warming.
(d) 2.5 g of toltrazuril and 12.5 g of lactic acid are dissolved in 100 ml of triethanolamine, while warming and stirring.
(e) 10.0 g of toltrazuril is dissolved in 100 ml of monoethanolamine.

(f)

Toltrazuril: 5.0 g
Propylene glycol: 50.0 g
Sodium carbonate: 5.0 g
Water: to make up to 100 ml (g)

Toltrazuril: 5.0 g
Monoethanolamine: 10 g
N-methylpyrrolidone: to make up to 100 ml (h)

Toltrazuril: 2.5 g
Sodium carbonate: 5.0 g
Polyethylene glycol 200: to make up to 100 ml Toltrazuril is dissolved in the polyethylene glycol, with warming, and the sodium carbonate is suspended in the solution.

EXAMPLE 1

In vivo fish treatment

Fish which were heavily infested with ectoparasites were treated for 1 hour at 20° C. in 20 ml of water to which 10 ppm of toltrazuril had been added. Thereafter, the fish were sacrificed and their parasite infestation was checked. The following pattern was found:

| Number | Fish species | Parasite species | Observation on the parasite after 1 hour |
|---|---|---|---|
| 9 | Roach | *Dactylogyrus cornu* | Parasites on the bottom of the container severely damaged or dead, isolated damaged parasites on the gills |
| 15 | Carp (2–4 cm) | *Dactylogyrus vastator* | Parasites on the bottom of the container dead, damaged parasites in the gills |
| 4 | Eels (44–48 cm) | *Pseudodactylogyrus anguillae* | Treatment duration 2.5 hours; parasites damaged |

In vitro parasite treatment

Parasites of the species mentioned were introduced into 150 ml of water at 20° C., to which the stated concentration of toltrazuril had been added, in a glass dish. After the stated time, the parasites were investigated under an optical microscope. The following observations were made:

| Parasite | Concentration/time | Observation on the parasite |
|---|---|---|
| Diplozoon-paradoxum | 5 ppm/55 minutes | dead |
| Diplozoon-paradoxum | 10 ppm/4 minutes | dead |
| Myxosoma sp. | 20 ppm/4.5 hours | parasite fatally damaged |

It will be understood that the specification and examples are illustrative but not limitative of the present invention and that other embodiments within the spirit and scope of the invention will suggest themselves to those skilled in the art.

What is claimed is:

1. A method of combating in fish an ectoparasite selected from the group consisting of ciliates, myxosporidiae, and the phylum plathelminthes, monogenea, which comprises applying to fish in need of treatment an amount effective to combat said ectoparasites of a triazinetrione of the formula

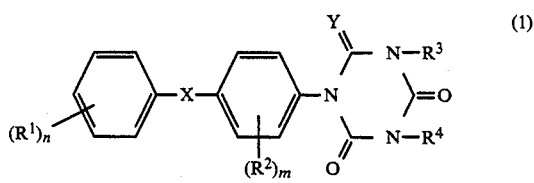

in which
X is O or S,
Y is O or S,
$R^1$ and $R^2$ each independently is a radical selected from the group consisting of halogen, nitro, CN, amino, $C_1$-$C_4$-alkyl, $C_1$-$C_4$-halogenoalkyl, $C_1$-$C_4$-alkoxy, methylenedioxy, $C_1$-$C_4$-halogenoalkoxy, $C_1$-$C_4$-alkylthio, $C_1$-$C_4$-halogenoalkylthio, $C_1$-$C_4$-alkylsulphonyl, $C_1$-$C_4$-alkylsulphinyl, $C_1$-$C_4$-halogenoalkylsulphonyl, $C_1$-$C_4$-halogenoalkylsulphinyl, $C_1$-$C_4$-acyl, benzoyl, carboxy, carbonylamino, $C_1$-$C_4$-carbonylalkoxy, carbamoyl and sulphamoyl, n and m each independently is an integer from 0 to 3, and
$R^3$ and $R^4$ each independently is hydrogen or $C_1$-$C_4$-alkyl.

2. The method according to claim 1, in which
X and Y each is O,
$R^1$ and $R^2$ each independently is a radical selected from the group consisting of halogen, nitro, CN, amino, $C_{1-4}$-alkyl, $C_{1-4}$-halogenoalkyl, $C_{1-4}$-alkoxy, methylenedioxy, $C_{1-4}$-halogenoalkoxy, $C_{1-4}$-alkylthio, $C_{1-4}$-halogenoalkylthio, $C_{1-4}$-alkylsulphonyl, $C_{1-4}$-alkylsulphinyl, $C_{1-4}$-halogenoalkylsulphonyl and -sulphinyl, $C_{1-4}$-acyl, benzoyl, and $C_{1-4}$-carbonylalkoxy,
n and m each independently is an integer from 0 to 2, and
$R^3$ and $R^4$ each independently is hydrogen or $C_{1-4}$-alkyl.

3. The method according to claim 1, in which
$R^4$ is hydrogen,
$R^3$ is $C_{1-4}$-alkyl,
Y is O or S,
X is O,
$R^2$ each independently is a radical selected from the group consisting of $C_{1-4}$-alkyl, halogen, $C_{1-4}$-alkoxy and $C_{1-2}$-halogenalkyl,
$R^1$ each independently is a radical selected from the group consisting of halogen; $NO_2$; $C_{1-4}$-alkyl; $C_{1-2}$-halogenoalkyl; $C_{1-4}$-alkylmercapto which is optionally substituted by halogen; $C_{1-4}$-alkoxy which is optionally substituted by halogen; $C_{1-4}$-alkylsulphinyl which is optionally substituted by halogen; and $C_{1-4}$-alkylsulphonyl which is optionally substituted by halogen, and
n and m each independently is an integer from 0 to 2.

4. A method according to claim 1, in which
$R^4$ is hydrogen,
$R^3$ is methyl,
X and Y each is O,
$R^2$ is a radical selected from the group consisting of chlorine, bromine, methyl, trifluoromethyl, methoxy and ethoxy,
$R^1$ is a radical selected from the group consisting of trifluoromethylmercapto, trifluoromethylsulphinyl, trifluoromethylsulphonyl and trifluoromethoxy, and
n and m independently of one another are 0 or 1.

5. A method according to claim 1, wherein the triazinetrione is 1-[3-methyl-4-(4'-trifluoromethylthiophenoxy)-phenyl]-3-methyl-1,3,5-triazine-2,4,6(1H,3H,5H)-trione.

* * * * *